(12) United States Patent
Johnson et al.

(10) Patent No.: US 6,787,549 B2
(45) Date of Patent: Sep. 7, 2004

(54) CITRATE SALT OF 5,8,14-TRIAZATETRACYCLO[10.3.1.0$^{2,11}$.0$^{4,9}$]-HEXADECA-2(11),3,5,7,9-PENTAENE AND PHARMACEUTICAL COMPOSITIONS THEREOF

(75) Inventors: Phillip J. Johnson, North Stonington, CT (US); Peter R. Rose, Ledyard, CT (US); Glenn R. Williams, East Aurora, NY (US); Lewin T. Wint, Wilmette, IL (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/139,449

(22) Filed: May 6, 2002

(65) Prior Publication Data

US 2003/0149091 A1 Aug. 7, 2003

Related U.S. Application Data

(60) Provisional application No. 60/290,863, filed on May 14, 2001.

(51) Int. Cl.$^7$ .................. C07D 471/08; A61K 31/4995
(52) U.S. Cl. ....................................... 514/250; 544/343
(58) Field of Search .......................... 544/343; 514/250, 514/214.03; 540/578

(56) References Cited

FOREIGN PATENT DOCUMENTS

EP        1078637      8/2000
WO     WO9935131      7/1999

*Primary Examiner*—Bruck Kifle
(74) *Attorney, Agent, or Firm*—P. C. Richardson; P. H. Ginsburg; A. D. Joran

(57) ABSTRACT

The present invention is directed to the citrate salt of 5,8,14-triazatetracyclo[10.3.1.0$^{2,11}$.0$^{4,9}$]-hexadeca-2(11),3,5,7,9-pentaene:

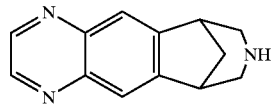

and pharmaceutical compositions thereof. The present invention is also directed to the various forms of the citrate salt, particularly its hydrate and its anhydrous/nearly anhydrous polymorph. The invention is also directed to processes for preparation of these citrate salt forms.

36 Claims, 10 Drawing Sheets

CITRATE SALT OF 5,8,14-TRIAZATETRACYCLO[10.3.1.0$^{2,11}$.0$^{4,9}$]-HEXADECA-2(11),3,5,7,9-PENTAENE AND PHARMACEUTICAL COMPOSITIONS THEREOF

This application claims the benefit of U.S. Provisional Application Ser. No. 60/290,863, filed May 14, 2001.

The present invention is directed to the citrate salt of 5,8,14-triazatetracyclo[10.3.1.0$^{2,11}$.0$^{4,9}$]-hexadeca-2(11),3,5,7,9-pentaene

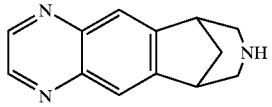

and pharmaceutical compositions thereof. The present invention is also directed to the various forms of the citrate salt, including its hydrate (referred to herein as Form A) and another polymorph that is an anhydrous or nearly anhydrous form (referred to herein as Form B).

The compound, 5,8,14-triazatetracyclo[10.3.1.0$^{2,11}$.0$^{4,9}$]-hexadeca-2(11),3,5,7,9-pentaene, binds to neuronal nicotinic acetylcholine specific receptor sites and is useful in modulating cholinergic function. This compound is useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy.

The citrate salts of this invention may also be used in a pharmaceutical composition in combination with an antidepressant such as, for example, a tricyclic antidepressant or a serotonin reuptake inhibiting antidepressant (SRI), in order to treat both the cognitive decline and depression associated with AD, PD, stroke, Huntington's chorea or traumatic brain injury (TBI); in combination with muscarinic agonists in order to stimulate both central muscarinic and nicotinic receptors for the treatment, for example, of ALS, cognitive dysfunction, age-related cognitive decline, AD, PD, stroke, Huntington's chorea and TBI; in combination with neurotrophic factors such as NGF in order to maximize cholinergic enhancement for the treatment, for example, of ALS, cognitive dysfunction, age-related cognitive decline, AD, PD stroke, Huntington's chorea and TBI; or in combination with agents that slow or arrest AD such as cognition enhancers, amyloid aggregation inhibitors, secretase inhibitors, tau kinase inhibitors, neuronal anti-inflammatory agents and estrogen-like therapy.

Compounds that bind to neuronal nicotinic receptor sites, including 5,8,14-triazatetracyclo[10.3.1.0$^{2,11}$.0$^{4,9}$]-hexadeca-2(11),3,5,7,9-pentaene, and its hydrochloride salt, are referred to in WO 99/35131, published Jul. 15, 1999 (corresponding to U.S. Ser. Nos. 09/402,010, filed Sep. 28, 1999 and 09/514,002, filed Feb. 25, 2000). The foregoing applications, owned in common with the present application and incorporated herein by reference in their entirety, generically recite pharmaceutically acceptable acid addition salts for the compounds referred to therein.

The citrate salt of the present invention exhibits properties, including those of solid-state stability and compatibility with certain drug product formulation excipients, that render it superior to previously known salts of 5,8,14-triazatetracyclo[10.3.1.0$^{2,11}$.0$^{4,9}$]-hexadeca-2(11),3,5,7,9-pentaene.

SUMMARY OF THE INVENTION

Figure 1:
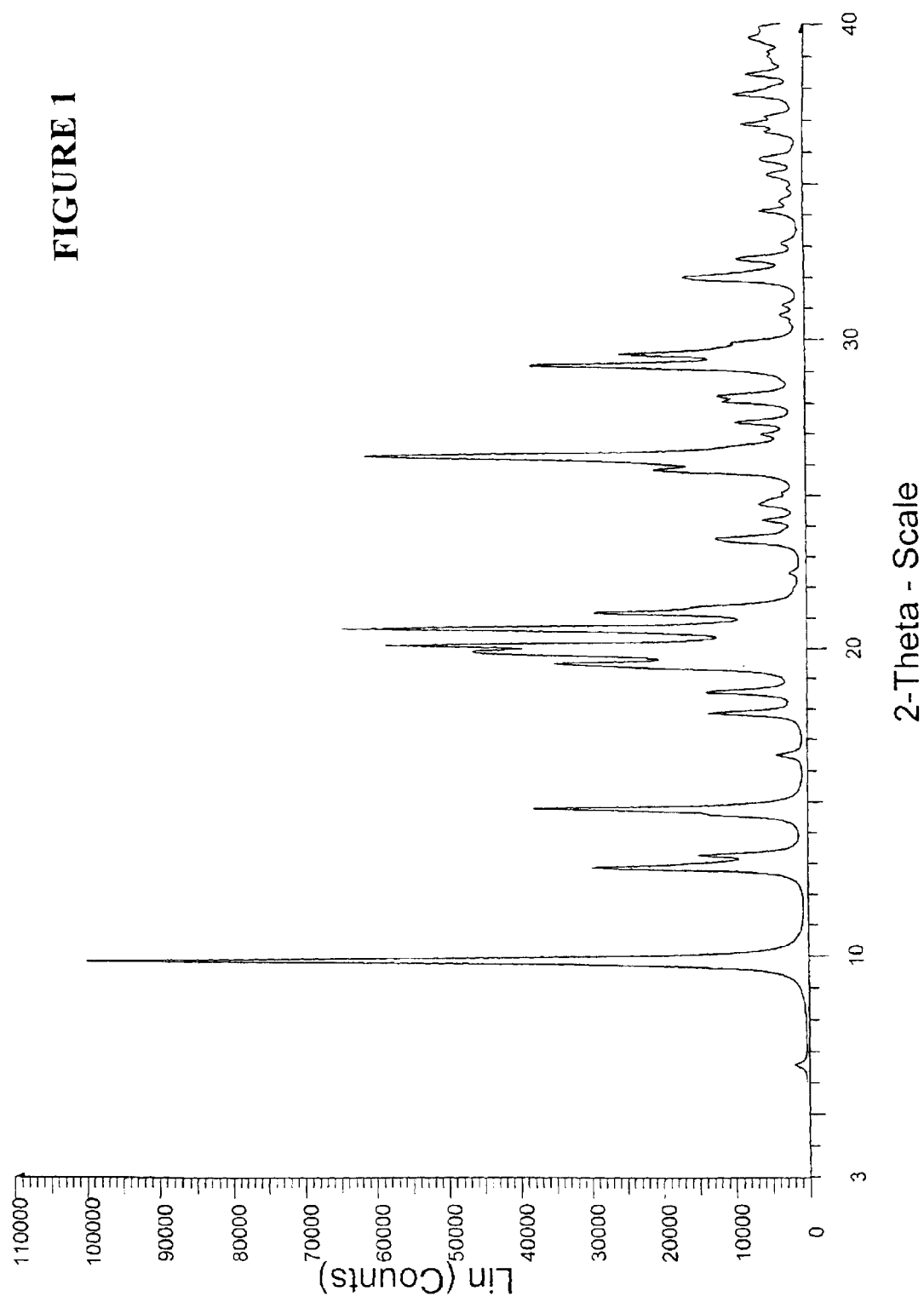
FIG. 1 is the calculated powder X-ray diffraction pattern of the citrate salt hydrate of 5,8,14-triazatetracyclo[10.3.1.0$^{2,11}$.0$^{4,9}$]-hexadeca-2(11),3,5,7,9-pentaene (Form A) (y axis is linear counts per second; X in degrees 2 theta).

The present invention relates to the citrate salt of 5,8,14-triazatetracyclo[10.3.1.0$^{2,11}$.0$^{4,9}$]-hexadeca-2(11),3,5,7,9-pentaene.

In a preferred embodiment of the invention, the citrate of 5,8,14-triazatetracyclo[10.3.1.0$^{2,11}$.0$^{4,9}$]-hexadeca-2(11),3,5,7,9-pentaene is the citrate salt hydrate, referred to herein as Form A. The term "hydrate" as referred to herein for Form A means that in the solid form there is between 1 and 5% water present by weight in the crystal and does not imply any stoichiometric relationship.

The citrate hydrate Form A is characterized by the principal x-ray diffraction pattern peaks expressed in terms of 2θ and d-spacings as measured with copper radiation (within the margins of error indicated):

| Angle 2θ (±0.2) | d-value (Å) (±0.2) |
|---|---|
| 9.7 | 9.1 |
| 12.8 | 6.9 |
| 14.6 | 6.1 |
| 19.7 | 4.5 |
| 20.0 | 4.4 |
| 20.5 | 4.3 |
| 26.1 | 3.4 |
| 29.1 | 3.1 |

The citrate hydrate Form A crystal is characterized in that it generally forms plates or prisms. Further, the citrate hydrate Form A is also characterized in that it forms triclinic crystals belonging to the P-1 space group. The citrate hydrate is further characterized in having an onset of melting transition/decomposition point at about 167° C. as measured by differential scanning calorimetry. Further, the citrate hydrate of the invention is also characterized in having an aqueous solubility of >100 mg/ml and a native pH of 3.7 in aqueous solution. In addition, the citrate hydrate has a hygroscopicity of approximately 0.6% at 90% relative humidity.

The citrate hydrate Form A crystal is also characterized in that when examined by solid state $^{13}$C NMR cross-polarization magic angle spinning techniques it exhibits the following principal resonance peaks downfield from 100 parts per million (±0.1 ppm; relative to an adamantane standard at 29.5 ppm): δ 179.8, 174.8, 173.7, 145.9, 141.8, 124.1, and 120.9 ppm. The citrate hydrate Form A in the solid state should at least exhibit the following principal resonance peaks downfield from 100 parts per million (±0.1 ppm; relative to an adamantane standard at 29.5 ppm): δ 179.8, 145.9 and 124.1 ppm.

In another embodiment of the invention, the citrate salt of 5,8,14-triazatetracyclo[10.3.1.0$^{2,11}$.0$^{4,9}$]-hexadeca-2(11),3,5,7,9-pentaene is an "anhydrous or nearly anhydrous" polymorph, referred to herein as Form B, formed when water is removed from the crystal lattice of Form A. The term "anhydrous or nearly anhydrous" polymorph as used herein with respect to Form B refers to a polymorph containing between 0 and 1% water by weight.

The citrate hydrate Form B is characterized by the principal x-ray diffraction pattern peaks expressed in terms of 2θ and d-spacings as measured with copper radiation (within the margins of error indicated:

| Angle 2θ (±0.2) | d-value (Å) (±0.2) |
|---|---|
| 9.9 | 9.0 |
| 12.9 | 6.8 |
| 14.6 | 6.1 |
| 19.7 | 4.5 |
| 20.5 | 4.3 |
| 26.1 | 3.4 |

The citrate salt Form B is further characterized in having an onset of melting transition/decomposition point at about 168° C. as measured by differential scanning calorimetry.

The citrate salt Form B crystal is also characterized in that when examined by solid state $^{13}$C NMR cross-polarization magic angle spinning techniques it exhibits the following principal resonance peaks downfield from 100 parts per million (±0.1 ppm; relative to an adamantane standard at 29.5 ppm): δ 180.0, 175.2, 173.1, 142.0, 139.5, 126.1, and 119.4 ppm. The citrate salt Form B in the solid state should at least exhibit the following principal resonance peaks downfield from 100 parts per million (±0.1 ppm; relative to an adamantane standard at 29.5 ppm): δ 180.0, 175.2, 173.1, 126.1 and 119.4 ppm.

Another embodiment of the invention relates to a pharmaceutical composition comprising the citrate salt of 5,8,14-triazatetracyclo[10.3.1.0$^{2,11}$.0$^{4,9}$]-hexadeca-2(11),3,5,7,9-pentaene, or at least one of polymorphic Forms A and B thereof, preferably Form A, and a pharmaceutically acceptable carrier or excipient, particularly, one for use in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), and Tourette's Syndrome. Another more preferred embodiment of the invention is wherein the pharmaceutical composition above is useful in the treatment of nicotine dependency, addiction and withdrawal; most preferably, for use in smoking cessation therapy.

The present invention further relates to a the method of treating inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), and Tourette's Syndrome comprises administering to a subject in need of treatment a therapeutically effective amount of the citrate salt of 5,8,14-triazatetracyclo[$10.3.1.0^{2,11}.0^{4,9}$]-hexadeca-2(11),3,5,7,9-pentaene, or either one of Form A or B thereof. Another more preferred embodiment of the invention relates to a method of treatment for nicotine dependency, addiction and withdrawal, in particular for use in smoking cessation therapy activity, comprising the administration of the citrate salt of 5,8,14-triazatetracyclo [$10.3.1.0^{2,11}.0^{4,9}$]-hexadeca-2(11),3,5,7,9-pentaene, or either one of Form A or B thereof, preferably Form A, to a subject in need thereof.

The invention also relates to a process for the preparation of Form A of the citrate salt of 5,8,14-triazatetracyclo [$10.3.1.0^{2,11}.0^{4,9}$]-hexadeca-2(11),3,5,7,9-pentaene comprising the steps of (i) contacting 5,8,14-triazatetracyclo[$10.3.1.0^{2,11}.0^{4,9}$]-hexadeca-2(11),3,5,7,9-pentaene in a suitable solvent with citric acid; and (ii) collecting the crystals formed.

A preferred embodiment is wherein the suitable solvent is selected from the group consisting of a ($C_1$–$C_6$)alkyl alcohol, a ($C_1$–$C_6$)alkyl ketone or a ($C_1$–$C_6$)alkyl ether in the presence of water. More preferably, the suitable solvent is a mixture of acetone and water or 2-propanol and water. Most preferably, the suitable solvent is a mixture of 2-propanol and water. Preferably, the process of the invention is wherein the contacting of step (i) is carried out by contacting 5,8,14-triazatetracyclo[$10.3.1.0^{2,11}.0^{4,9}$]-hexadeca-2(11),3,5,7,9-pentaene in solution phase with a solution of citric acid. Preferably, the contacting step is carried out over a period of between 1 and 24 hours, more preferably between 5 and 15 hours, and comprising stirring or mixing the resulting mixture. A preferred embodiment of the process is wherein step (i) is run between ambient temperature and the refluxing temperature of the solvent; more preferably, between ambient temperature and the refluxing temperature of 2-propanol, i.e., about 80° C.; most preferably, the process in run between 30 and 60° C.

The invention also relates to a process for the preparation of Form B of the citrate salt of 5,8,14-triazatetracyclo [$10.3.1.0^{2,11}.0^{4,9}$]-hexadeca-2(11),3,5,7,9-pentaene comprising the steps of (i) contacting 5,8,14-triazatetracyclo[$10.3.1.0^{2,11}.0^{4,9}$]-hexadeca-2(11),3,5,7,9-pentaene in an anhydrous suitable solvent with citric acid; and (ii) collecting the crystals formed.

A preferred embodiment for preparing Form B is wherein the anhydrous suitable solvent is selected from the group consisting of an anhydrous ($C_1$–$C_6$)alkyl alcohol, an anhydrous ($C_1$–$C_6$)alkyl ketone or an anhydrous ($C_1$–$C_6$)alkyl ether. More preferably, the suitable solvent is anhydrous methanol, anhydrous ethanol or anhydrous 2-propanol.

The invention also relates to a process for the preparation of Form B of the citrate salt of 5,8,14-triazatetracyclo [$10.3.1.0^{2,11}.0^{4,9}$]-hexadeca-2(11),3,5,7,9-pentaene comprising the step of drying the citrate salt hydrate of 5,8,14-triazatetracyclo[$10.3.1.0^{2,11}.0^{4,9}$]-hexadeca-2(11),3,5,7,9-pentaene. In one embodiment, the drying is carried out by the steps of (i) reducing the particle size of the citrate hydrate of 5,8,14-triazatetracyclo[$10.3.1.0^{2,11}.0^{4,9}$]-hexadeca-2(11),3,5,7,9-pentaene; and (ii) drying the resultant solid from step (i) under vacuum. The particle size reduction in step (i) may be accomplished by jet milling, mechanical milling or other effective means of reducing particle size. Preferably, the drying step (ii) is conducted in the temperature range of between 20 and 60° C.

In another embodiment, the drying process for preparing Form B is carried out by dissolving Form A in an anhydrous solvent, preferably an anhydrous ($C_1$–$C_6$)alkyl alcohol, a ($C_1$–$C_6$)alkyl ketone, a ($C_1$–$C_6$)alkyl ether or any other suitable anhydrous solvent, driving off, if necessary the water as an azeotrope, and allowing Form B to crystallize from solution. In a further embodiment, the drying process is effectuated by heating Form A to 60 to 120° C. for between 30 minutes and 24 hours, preferably, for at least 12 hours.

DETAILED DESCRIPTION OF THE INVENTION

The compound, 5,8,14-triazatetracyclo[$10.3.1.0^{2,11}.0^{4,9}$]-hexadeca-2(11),3,5,7,9-pentaene is a nicotinic partial agonist for the treatment of a number of CNS diseases, disorders and conditions including, in particular, nicotine dependency, addiction and withdrawal.

The citrate salt hydrate of 5,8,14-triazatetracyclo [$10.3.1.0^{2,11}.0^{4,9}$]-hexadeca-2(11),3,5,7,9-pentaene, Form A, is only slightly hygroscopic and has high aqueous solubility. These characteristics combined with its relative inertness towards common excipients used in pharmaceutical formulation make it highly suitable for pharmaceutical formulation use.

Although in general the acid addition salts of 5,8,14-triazatetracyclo[$10.3.1.0^{2,11}.0^{4,9}$]-hexadeca-2(11),3,5,7,9-pentaene are all crystalline, the majority of those salts are so hygroscopic as to render them poor candidates for pharmaceutical formulation use. The citrate salt exists as a hydrate under ambient conditions, where as noted above, hydrate refers to a water content of between 1 and 5% water by weight in the crystal. The citrate hydrate salt Form A of the present invention exhibits a hygroscopicity of approximately 0.6% wt/wt on exposure to 90% relative humidity in a moisture chamber. The aqueous solubility of the citrate hydrate salt is 110 mg/ml. Further, the citrate hydrate salt of 5,8,14-triazatetracyclo[10.3.1.0$^{2,11}$.0$^{4,9}$]-hexadeca-2(11),3, 5,7,9-pentaene exhibits excellent solid state stability both in light and elevated temperatures as well as high humidity challenges. The citrate salt hydrate Form A has been prepared under different conditions:

Acetone Method: The 5,8,14-triazatetracyclo [10.3.1.0$^{2,11}$.0$^{4,9}$]-hexadeca-2(11),3,5,7,9-pentaene dissolved in a 50/50 acetone/water mixture is added to a citric acid solution in 50/50 acetone/water. A slurry is formed and allowed to stir at 20 to 25° C. for approximately 24 hours. The product crystallizes on agitation to give the desired hydrate isolated as the solvent wet cake, usually in approximately 85% yield. The product crystals are small and generally agglomerated or aggregated together.

2-Propanol/water Method: This procedure is appropriate for 2-propanol/water mixtures in the range from 50/50 to 90/10 (v/v). The preparation of the citrate hydrate form of 5,8,14-triazatetracyclo[10.3.1.0$^{2,11}$.0$^{4,9}$]-hexadeca-2(11),3,5,7,9-pentaene was carried out by adding to a 2-propanol/water solution of 5,8,14-triazatetracyclo[10.3.1.0$^{2,11}$.0$^{4,9}$]-hexadeca-2(11),3,5, 7,9-pentaene a citric acid solution 2-propanol and water and stirred at 20 to 25° C. until dissolved. The solution was held at 45 to 55° C. for several hours, preferably between 2 and 5 hours. The mixture was cooled over 1 to 4 hours to 0 to 5° C. In general, large prismatic crystals were isolated, with thick plate-like crystals also being observed, which were significantly larger and better formed than those from acetone-water procedure above.

Under low humidity and elevated temperature, Form A will lose water depending on the macroscopic crystalline form. Unmilled samples of Form A may be dried in a 45° C. vacuum oven for several days without significant water loss (<1% water loss). However, micronized samples of Form A readily lose and regain water as humidity and temperature are varied. Under conditions of low humidity and heat, Form A will dehydrate completely or nearly so to form a distinct pseudomorph which maintains a crystalline lattice, referred to herein as Form B. Form B contains between 0 and 1% water by weight.

Form B can be prepared independently in a similar manner to that by which Form A is made with the exception of using an anhydrous solvent. Preferably, a solvent such as anhydrous methanol, anhydrous ethanol or anhydrous 2-propanol is useful.

Form B of the citrate salt of 5,8,14-triazatetracyclo [10.3.1.0$^{2,11}$.0$^{4,9}$]-hexadeca-2(11),3,5,7,9-pentaene can also be prepared by drying the citrate salt hydrate of 5,8,14-triazatetracyclo[10.3.1.0$^{2,11}$.0$^{4,9}$]-hexadeca-2(11),3,5,7,9-pentaene. A number of means for drying the water from the crystal lattice may be employed. Form B may be prepared by reducing the particle size of Form A, via any technique known to those of skill in the art, including jet milling, mechanical milling, etc., and drying the reduce particle size citrate salt Form A under conditions sufficient to remove the water in the lattice. The particle size reduced citrate hydrate Form A shows water loss after less than 1 hour at 45° C. and during the drying cycles (vacuum, dry N$_2$) in a moisture balance system. Vacuum drying at temperatures in the range of 20 to 60° C. will yield Form B in the course of 30 minutes to 10 hours.

Alternatively, the drying of Form A to prepare Form B may also carried out by dissolving Form A in an anhydrous solvent, preferably an anhydrous (C$_1$–C$_6$)alkyl alcohol, a (C$_1$–C$_6$)alkyl ketone, a (C$_1$–C$_6$)alkyl ether or any other suitable anhydrous solvent (and if necessary, driving off the water present from the crystal now dissolved in the solvent as an azeotrope), and then allowing Form B to crystallize from solution. In a further embodiment, the drying process is effectuated by simply by heating Form A to 60 to 120° C. for between 30 minutes and 24 hours, preferably, for at least 12 hours.

Differential Scanning Calorimetry

Figure 9:
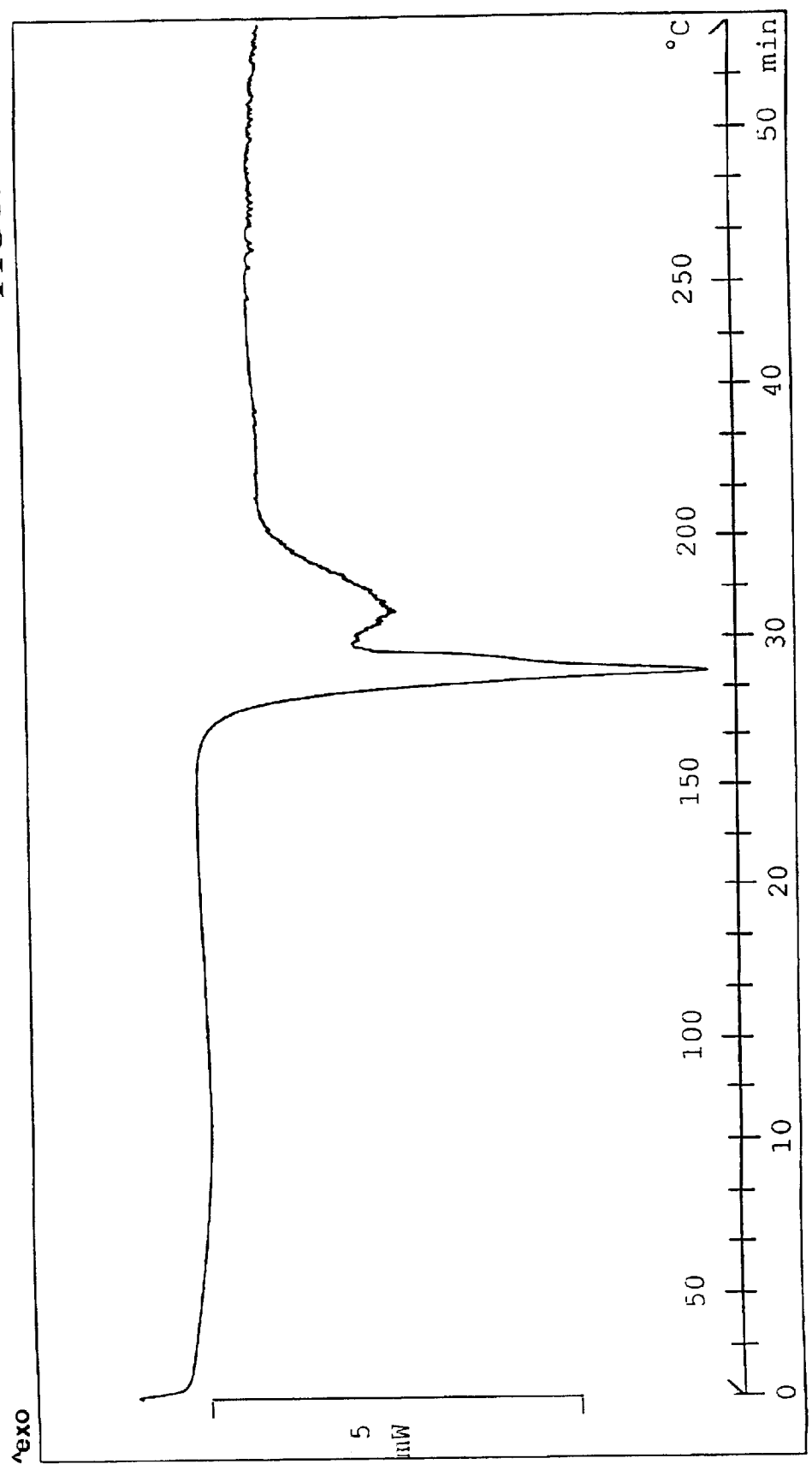
FIG. 9 is the differential scanning calorimetric trace of the citrate salt hydrate of 5,8,14-triazatetracyclo[10.3.1.0$^{2,11}$.0$^{4,9}$]-hexadeca-2(11),3,5,7,9-pentaene (Form A).
Figure 10:
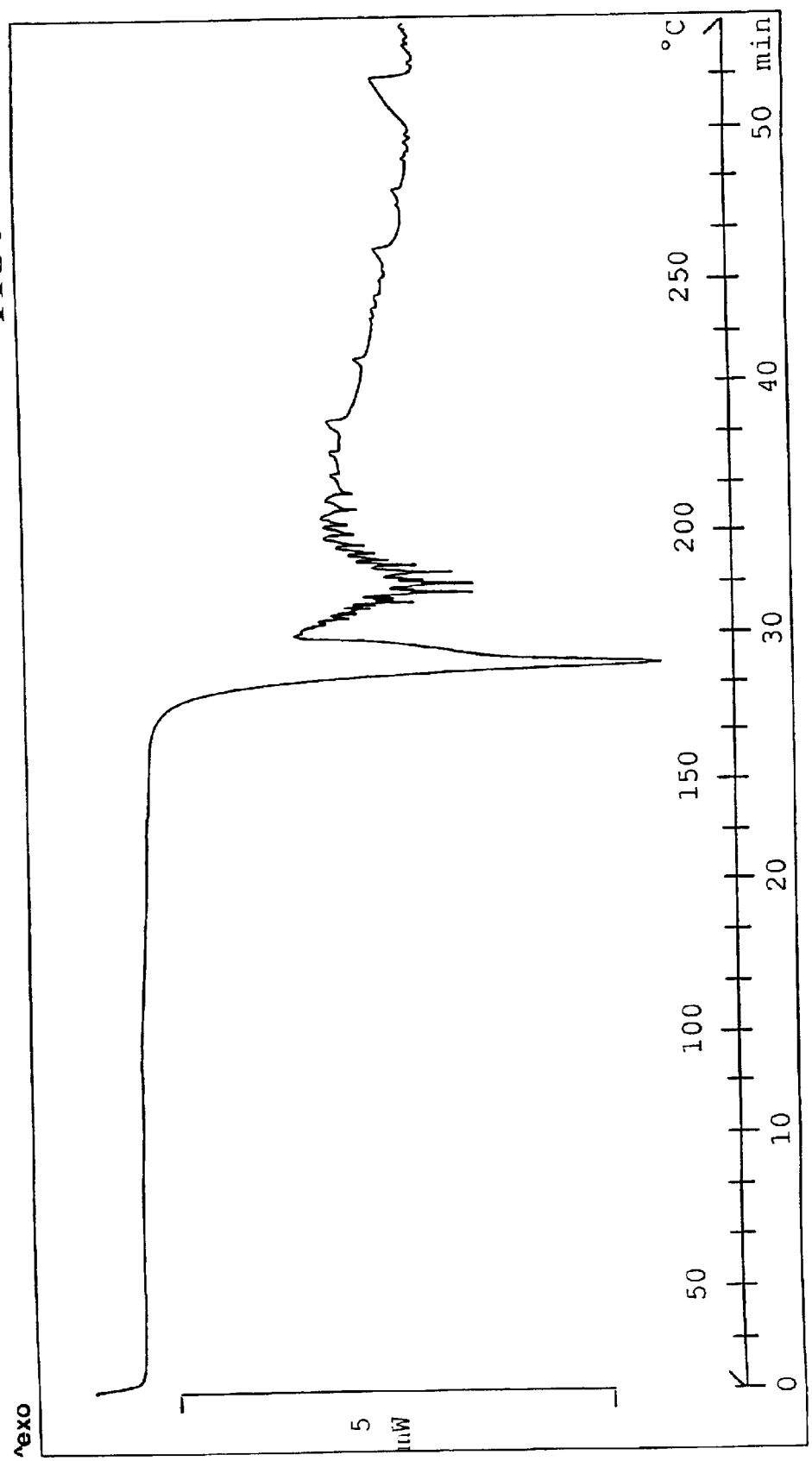
FIG. 10 is the differential scanning calorimetric trace of the anhydrous or nearly anhydrous citrate salt of 5,8,14-triazatetracyclo[10.3.1.0$^{2,11}$.0$^{4,9}$]-hexadeca-2(11),3,5,7,9-pentaene (Form B).

The solid state thermal behavior of both Forms A and B were investigated by differential scanning calorimetry (DSC). The traces for Forms A and B are shown in FIGS. 9 and 10 respectively. The DSC thermograms were obtained on a Mettler Toledo DSC 821$^e$ (STAR$^e$ System). Generally, samples between 1 and 10 mg were prepared in crimped aluminum pans with a small pinhole. The measurements were run at a heating rate of 5° C. per minute in the range of 30 to 300° C.

As seen in FIG. 9, the citrate salt hydrate Form A exhibits onset of melt transition at about 167–8° C. and is accompanied by decomposition. In actuality, the act of heating Form A results in its dehydration, and hence formation of Form B, by the time it has reached the melting transition point. Accordingly, the melt transition observed in FIG. 9 is actually that of Form B formed in situ from the initial Form A sample. As seen in FIG. 10, when measuring an actual sample of the citrate salt Form B by DSC, there is observed an onset of melt transition accompanied by decomposition at about 167–8° C., like that seen for Form A. One of skill in the art will however note that in DSC measurement there is a certain degree of variability in actual measured onset and peak temperatures which occur depending on rate of heating, crystal shape and purity, and other measurement parameters.

Powder X-ray Diffraction Patterns

The power x-ray diffraction patterns for both Forms A and B were collected using a Bruker D5000 diffractometer (Bruker AXS, Madison, Wis.) equipped with copper radiation CuK$_\alpha$, fixed slits (1.0, 1.0, 0.6 mm), and a Kevex solid state detector. Data was collected from 3.0 to 40.0 degrees in two theta (2θ) using a step size of 0.04 degrees and a step time of 1.0 seconds.

The x-ray powder diffraction pattern of the hydrate citrate salt Form A was conducted with a copper anode with wavelength 1 at 1.54056 and wavelength 2 at 1.54439 (relative intensity: 0.500). The range for 2θ was between 3.0 to 40.0 degrees with a step size of 0.04 degrees, a step time of 1.00 second, a smoothing width of 0.300 and a threshold of 1.0.

Figure 2:
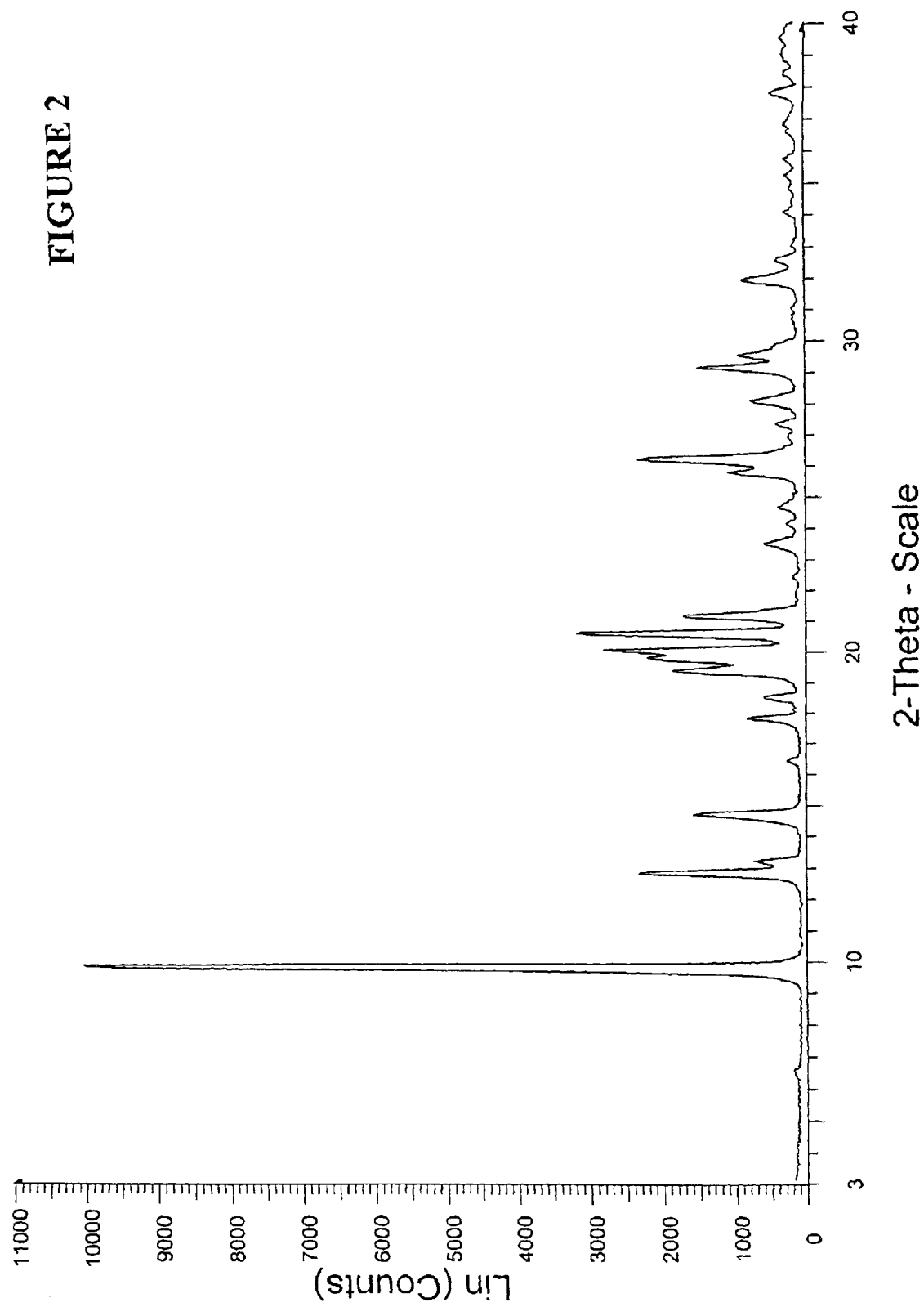
FIG. 2 is the observed powder X-ray diffraction pattern of the citrate salt hydrate of 5,8,14-triazatetracyclo[10.3.1.0$^{2,11}$.0$^{4,9}$]-hexadeca-2(11),3,5,7,9-pentaene (Form A) (y axis is linear counts per second; X in degrees 2 theta).

The diffraction peaks at diffraction angles (2θ) in a measured powder X-ray diffraction analysis for the Form A are shown in Table I. The relative intensities, however, may change depending on the crystal size and morphology. The actual measured powder diffractogram is displayed in FIG. 2.

TABLE I

Powder X-ray Diffraction Pattern for Form A with Intensities and Peak Locations of Diffraction Lines.

| Angle 2θ | d-value (Å) | I (rel.) |
|---|---|---|
| 9.7 | 9.1 | 100.0 |
| 12.8 | 6.9 | 23.1 |
| 13.1 | 6.8 | 7.2 |
| 14.6 | 6.1 | 15.6 |
| 16.3 | 5.4 | 2.5 |

TABLE I-continued

Powder X-ray Diffraction Pattern for Form A
with Intensities and Peak Locations of Diffraction Lines.

| Angle 2θ | d-value (Å) | I (rel.) |
|---|---|---|
| 17.7 | 5.0 | 8.1 |
| 18.4 | 4.8 | 5.6 |
| 19.3 | 4.6 | 18.4 |
| 19.7 | 4.5 | 21.8 |
| 20.0 | 4.4 | 27.7 |
| 20.5 | 4.3 | 31.4 |
| 21.1 | 4.2 | 16.9 |
| 23.4 | 3.8 | 5.6 |
| 24.1 | 3.7 | 2.5 |
| 24.6 | 3.6 | 3.7 |
| 25.7 | 3.5 | 10.7 |
| 26.1 | 3.4 | 23.1 |
| 27.3 | 3.3 | 3.9 |
| 28.0 | 3.2 | 7.5 |
| 29.1 | 3.1 | 14.9 |
| 29.5 | 3.0 | 9.3 |
| 29.8 | 3.0 | 3.9 |
| 31.9 | 2.8 | 8.7 |
| 32.5 | 2.8 | 3.9 |
| 34.0 | 2.6 | 2.6 |
| 35.2 | 2.5 | 2.5 |
| 35.7 | 2.5 | 2.6 |
| 36.8 | 2.4 | 2.6 |
| 37.8 | 2.4 | 4.7 |
| 38.4 | 2.3 | 2.6 |
| 38.9 | 2.3 | 2.9 |
| 39.5 | 2.3 | 3.2 |
| 39.8 | 2.3 | 2.5 |

Table II sets forth the 2θ, d-spacings and relative intensities and peak locations for the powder x-ray diffraction pattern representative for Form A. The numbers as listed are computer-generated.

TABLE II

Powder X-ray Diffraction Intensities and Peak Locations
Representative of Form A.

| Angle 2θ | d-value (Å) | I (rel.) |
|---|---|---|
| 9.7 | 9.1 | 100.0 |
| 12.8 | 6.9 | 23.1 |
| 14.6 | 6.1 | 15.6 |
| 19.7 | 4.5 | 21.8 |
| 20.0 | 4.4 | 27.7 |
| 20.5 | 4.3 | 31.4 |
| 26.1 | 3.4 | 23.1 |
| 29.1 | 3.1 | 14.9 |

Figure 4:
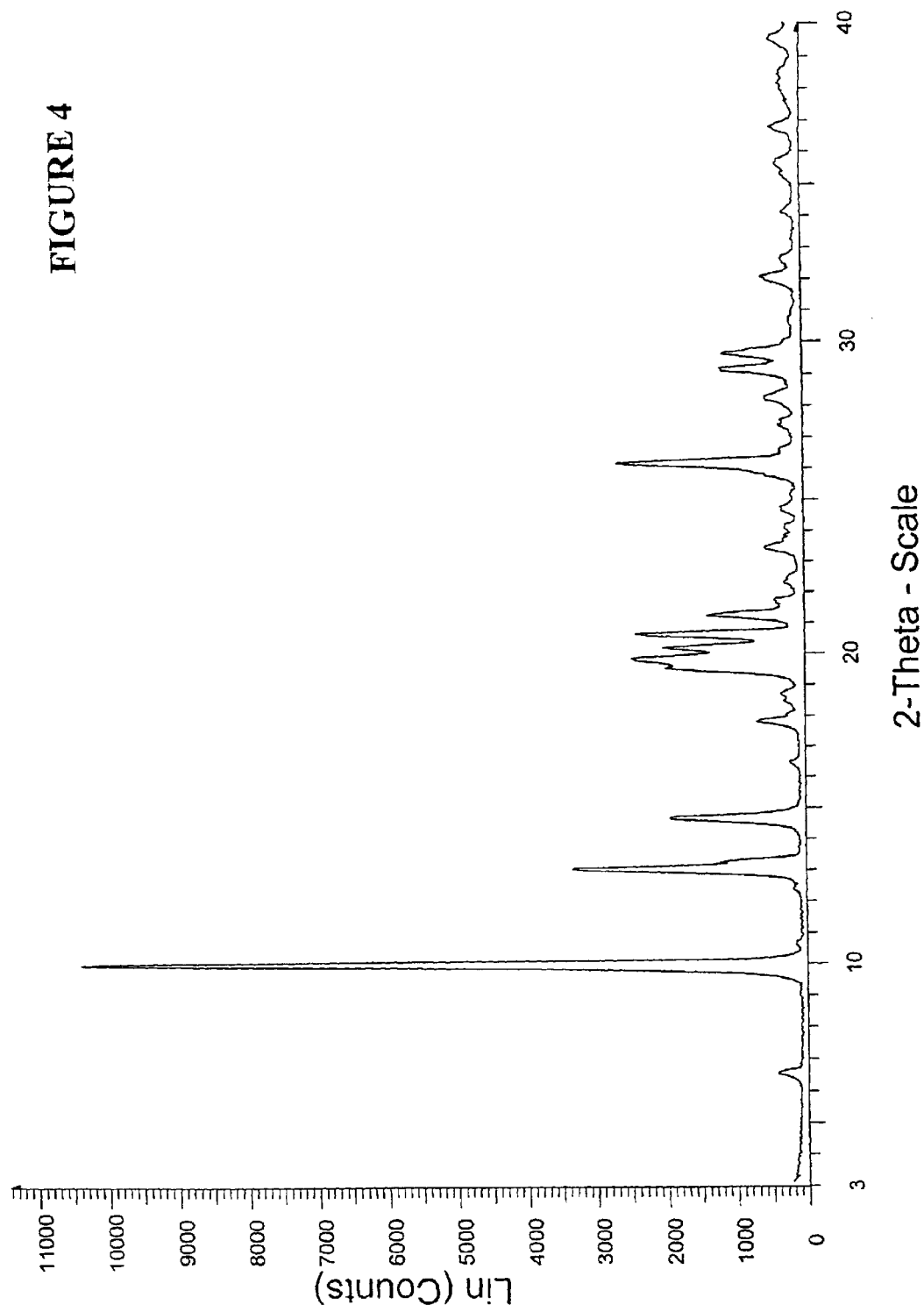
FIG. 4 is the observed powder X-ray diffraction of the dehydrated anhydrous or nearly anhydrous citrate salt of 5,8,14-triazatetra-cyclo[10.3.1.0$^{2,11}$.0$^{4,9}$]-hexadeca-2(11),3,5,7,9-pentaene (Form B) (y axis is linear counts per second; X in degrees 2 theta).

The x-ray powder diffraction pattern of the citrate salt Form B was measured with the same equipment and under that same parameters used above for the measurement of Form A. The diffraction peaks at diffraction angles (2θ) in a measured powder X-ray diffraction analysis for the Form B are shown in Table III. Again, the relative intensities, however, may change depending on the crystal size and morphology. The actual measured powder diffractogram is displayed in FIG. 4.

TABLE III

Powder X-ray Diffraction Pattern for Form B with Intensities
and Peak Locations of Diffraction Lines.

| Angle 2θ | d-value (Å) | I (rel.) |
|---|---|---|
| 6.4 | 13.7 | 3.9 |
| 9.9 | 9.0 | 100.0 |
| 12.9 | 6.8 | 32.1 |
| 14.6 | 6.1 | 18.5 |
| 17.7 | 5.0 | 6.4 |
| 18.4 | 4.8 | 2.7 |
| 18.6 | 4.8 | 3.0 |
| 19.5 | 4.6 | 19.1 |
| 19.7 | 4.5 | 23.7 |
| 20.1 | 4.4 | 19.4 |
| 20.5 | 4.3 | 23.1 |
| 21.2 | 4.2 | 13.1 |
| 21.6 | 4.1 | 3.9 |
| 22.2 | 4.0 | 2.5 |
| 23.4 | 3.8 | 5.2 |
| 24.0 | 3.7 | 2.5 |
| 24.6 | 3.6 | 3.0 |
| 26.1 | 3.4 | 25.6 |
| 26.6 | 3.4 | 3.0 |
| 27.3 | 3.3 | 3.2 |
| 28.2 | 3.2 | 4.9 |
| 29.1 | 3.1 | 11.1 |
| 29.6 | 3.0 | 10.8 |
| 32.0 | 2.8 | 5.4 |
| 32.6 | 2.7 | 2.6 |
| 35.3 | 2.5 | 2.5 |
| 35.6 | 2.5 | 3.2 |
| 36.7 | 2.4 | 4.0 |
| 38.2 | 2.4 | 2.8 |
| 38.4 | 2.3 | 2.8 |
| 39.5 | 2.3 | 4.1 |

Table IV sets forth the 2θ, d-spacings and relative intensities and peak locations for the powder x-ray diffraction pattern representative for Form B. The numbers as listed are computer-generated.

TABLE IV

Powder X-ray Diffraction Intensities and Peak Locations
Representative of Form B.

| Angle 2θ | d-value (Å) | I (rel.) |
|---|---|---|
| 9.9 | 9.0 | 100.0 |
| 12.9 | 6.8 | 32.1 |
| 14.6 | 6.1 | 18.5 |
| 19.7 | 4.5 | 23.7 |
| 20.5 | 4.3 | 23.1 |
| 26.1 | 3.4 | 25.6 |

Figure 5:
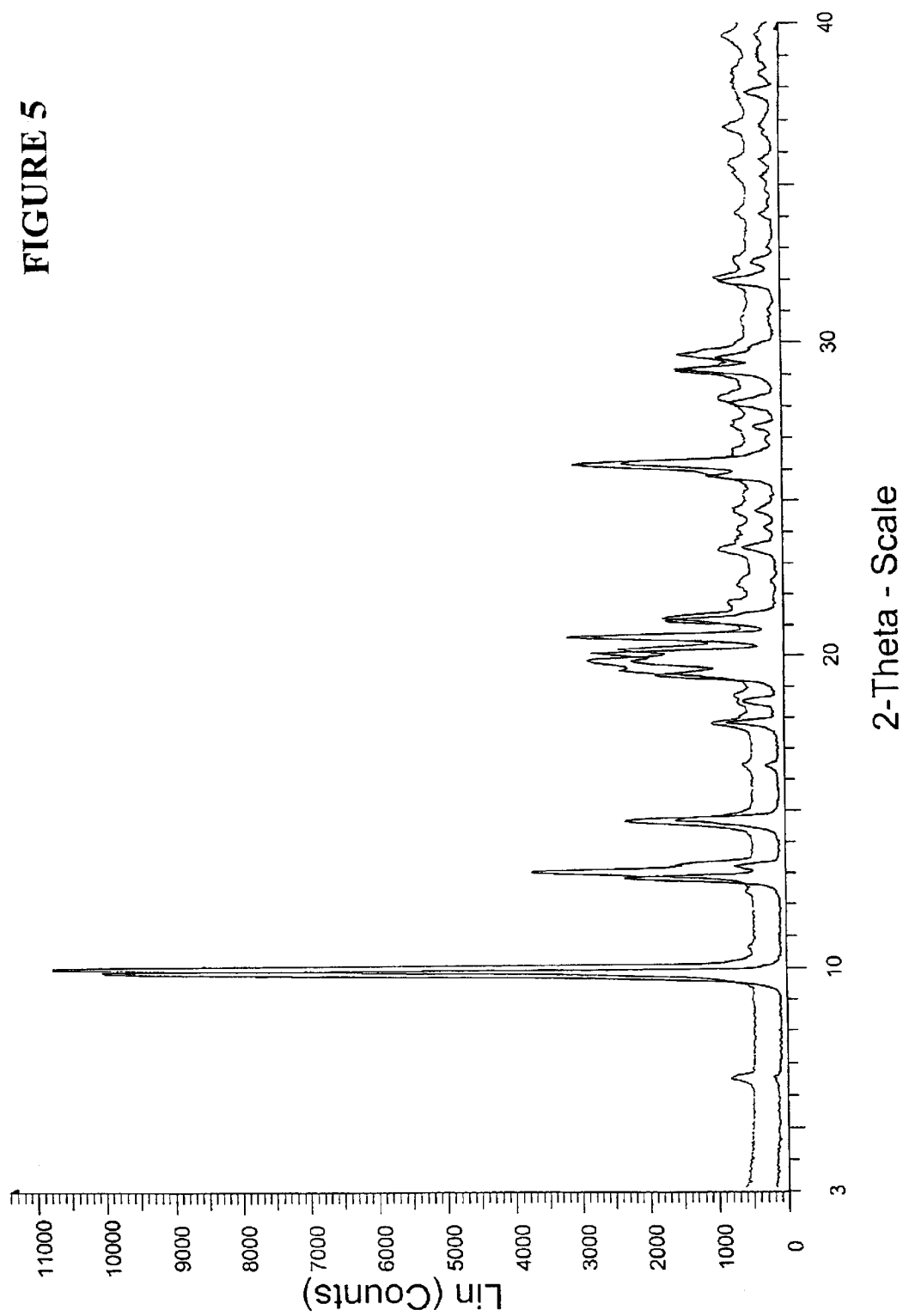
FIG. 5 is the observed powder X-ray diffraction of the citrate salt anhydrous or nearly anhydrous form of 5,8,14-triazatetra-cyclo[10.3.1.0$^{2,11}$.0$^{4,9}$]-hexadeca-2(11),3,5,7,9-pentaene (Form B) (upper trace) superimposed upon the observed powder X-ray diffraction of the citrate salt hydrate (Form A) (lower trace) (y axis is linear counts per second; X in degrees 2 theta).

As shown in FIG. 5, the overlay of the hydrate citrate salt Form A on that of the anhydrous or nearly anhydrous pseudomorph Form B shows some x-ray powder diffraction peak shifting.

Single Crystal X-ray Analysis

A single crystal for the citrate salt hydrate Form A was obtained and investigated by x-ray diffraction. A representative crystal was surveyed and a 1 Å data set (maximum sin Θ/λ=0.5) was collected on a Siemens R4RA/v diffractometer. Atomic scattering factors were taken from the *International Tables for X-Ray Crystallography*, Vol. IV, pp. 55, 99 and 149 (Birmingham: Kynoch Press, 1974) From the data gathered on the single crystal, a powder X-ray diffraction pattern for Form A was calculated to offer comparison against the actual measured diffraction pattern.

Structures were solved using direct methods. The SHELXTL™ computer library provided by Bruker AXS, Inc facilitated all necessary crystallographic computations and molecular displays (SHELXTL™ Reference Manual, Version 5.1, Bruker AXS, Madison, Wis. 1997). Pertinent crystal, data collection, and refinement are summarized in Table V.

Figure 8:
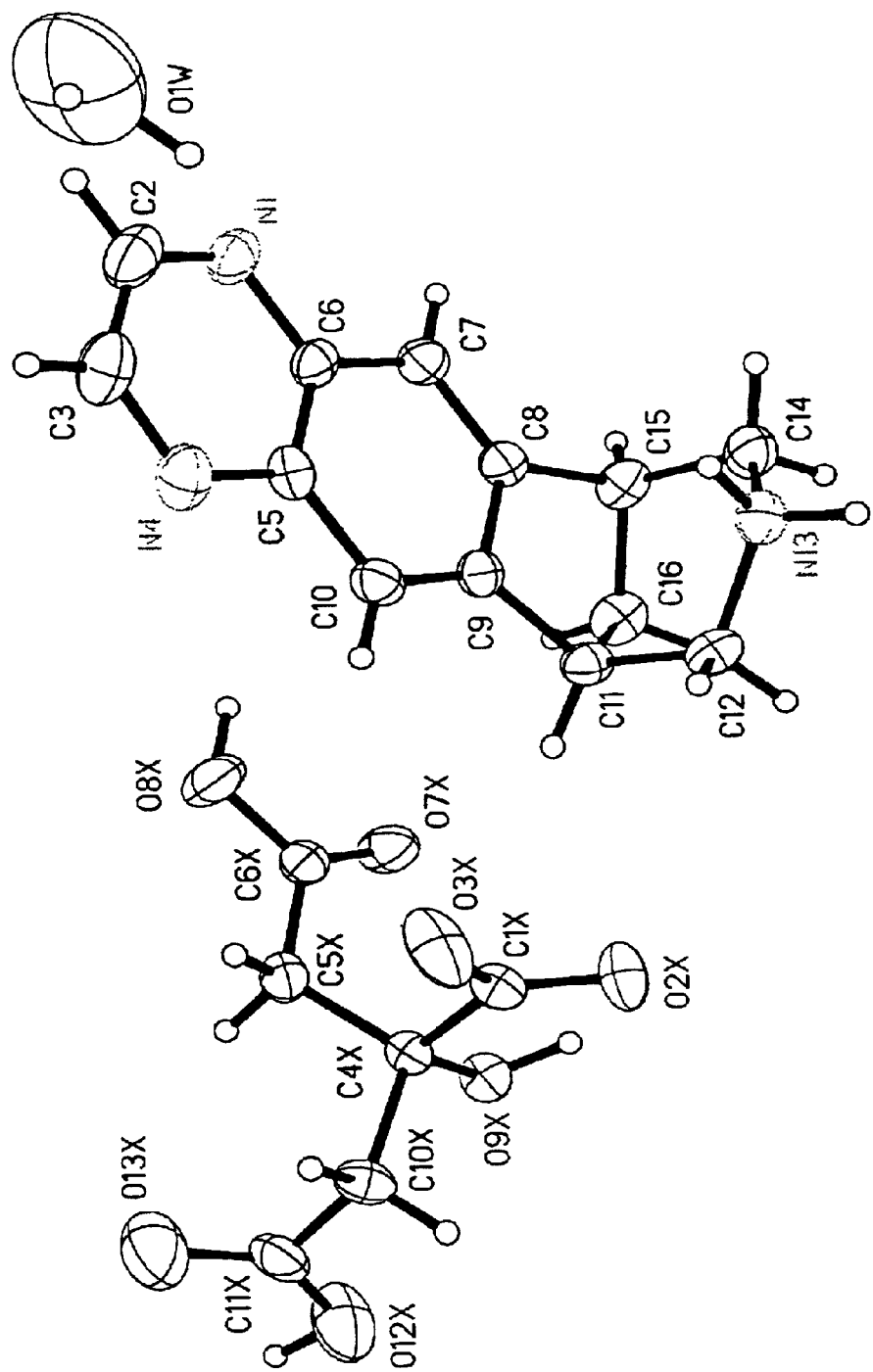
FIG. 8 is the X-ray crystal structure of the citrate salt hydrate (nonstoichiometric) of 5,8,14-triazatetracyclo[10.3.1.0$^{2,11}$.0$^{4,9}$]-hexadeca-2(11),3,5,7,9-pentaene (Form A).

A trial structure was obtained by direct methods and was then refined routinely. Hydrogen positions were calculated wherever possible. A difference map indicated that one of the carboxy groups (C11x, O12x, O13x) was slightly disordered. Attempts to fit this disorder did not prove practical (populations of 10%). Larger than usual thermal parameters were used to fit the disorder. The hydrogens on nitrogen and oxygen were located by difference Fourier techniques. The hydrogen parameters were added to the structure factor calculations but were not refined. The shifts calculated in the final cycles of least squares refinement were all less than 0.1 of the corresponding standard deviations. The final R-index was 5.31%. A final difference Fourier revealed no missing or misplaced electron density. The refined structure was plotted using the SHELXTL plotting package and is shown in FIG. 8.

Table VI sets forth the atomic coordinates ($\times 10^4$) and equivalent isotropic displacement parameters ($\text{Å}^2 \times 10^3$) for Form A. Table VII lists the observed bond lengths [Å] and angles [°] for Form A. In Table VIII, the anisotropic displacement parameters ($\text{Å}^2 \times 10^3$) for Form A are set forth to allow calculation of the anisotropic displacement factor exponent which has the form: $-2\pi^2[h^2 a^{*2} U_{11} + \ldots + 2h\,k\,a^* b^* U_{12}]$. Finally, in Table IX, below, hydrogen Coordinates ($\times 10^4$) and isotropic displacement parameters ($\text{Å}^2 \times 10^3$) for Form A are listed.

TABLE V

Crystal Structure Data And Measurement Parameters For Citrate Salt Hydrate Form A

| Parameter | For Citrate Salt Hydrate (Form A) |
|---|---|
| Crystal System | Triclinic |
| Space Group | P-1 |
| Crystal Size, mm | 0.08 × 0.30 × 0.22 |
| X-ray Code | F613 |
| a | 7.537Å |
| b | 9.687Å |
| c | 14.100Å |
| α | 99.61° |
| γ | 106.87° |
| β | 96.17° |
| Volume | 957.97Å$^3$ |
| Density calc'd, ρ | 1.461 g/cm$^3$ |
| Temperature | 293(2)K |
| Wavelength | 1.54178 Å |
| Z | 2 |
| Absorption coefficient | 0.976 mm$^{-1}$ |
| F(000) | 444 |
| Reflections collected | 2174 |
| Independent reflections | 1976 [R(int) = 0.0185] |
| Refinement method | Full-matrix least-squares on F$^2$ |
| Data/restraints/parameters | 1976/0/293 |
| Goodness-of-fit on F$^2$ | 0.966 |
| Final R indices [I > 2 sigma(I)] | R1 = 0.0531, wR2 = 0.1481 |
| Extinction coefficient | 0.0165(18) |
| Largest diff. peak and hole | 0.795 and −0.271 e.Å$^{-3}$ |
| Empirical formula | $C_{13}H_{14}N_3{}^+ C_6H_7O_7{}^- \cdot H_2O$ |
| Formula weight | 421.40 |

TABLE VI

Atomic coordinates ($\times 10^4$) And Equivalent Isotropic Displacement Parameters ($\text{Å}^2 \times 10^3$) For The Citrate Salt Hydrate. (U(eq) is defined as one third of the trace of the orthogonalized $U_{ij}$ tensor.)

|  | x | y | z | U(eq) |
|---|---|---|---|---|
| N(1) | −8404(4) | 4318(3) | −418(2) | 33(1) |
| C(2) | −9266(5) | 2945(5) | −858(3) | 41(1) |
| C(3) | −8934(6) | 1752(4) | −507(3) | 45(1) |
| N(4) | −7745(5) | 1936(3) | 290(2) | 40(1) |
| C(5) | −6864(5) | 3358(4) | 782(2) | 28(1) |
| C(6) | −7201(5) | 4558(4) | 434(2) | 26(1) |
| C(7) | −6353(5) | 6019(4) | 976(2) | 29(1) |
| C(8) | −5212(5) | 6231(4) | 1847(2) | 25(1) |
| C(9) | −4828(5) | 5031(4) | 2183(2) | 25(1) |
| C(10) | −5620(5) | 3616(4) | 1670(2) | 28(1) |
| C(11) | −3572(5) | 5628(4) | 3164(2) | 27(1) |
| C(12) | −4750(5) | 5657(4) | 3971(2) | 29(1) |
| N(13) | −6197(4) | 6404(3) | 3759(2) | 28(1) |
| C(14) | −5513(5) | 7795(4) | 3378(3) | 34(1) |
| C(15) | −4247(5) | 7616(4) | 2623(2) | 30(1) |
| C(16) | −2591(5) | 7222(4) | 3104(3) | 34(1) |
| C(1X) | −2081(5) | 2449(4) | 3907(3) | 24(1) |
| O(2X) | −1981(3) | 3429(3) | 4623(2) | 37(1) |
| O(3X) | −3539(3) | 1462(3) | 3460(2) | 51(1) |
| C(4X) | −229(4) | 2424(3) | 3550(2) | 21(1) |
| C(5X) | −370(5) | 2339(4) | 2450(2) | 30(1) |
| C(6X) | −477(5) | 3684(4) | 2067(3) | 27(1) |
| O(7X) | 300(4) | 4957(3) | 2486(2) | 39(1) |
| O(8X) | −1452(4) | 3334(3) | 1187(2) | 44(1) |
| O(9X) | 1258(3) | 3667(2) | 4078(2) | 27(1) |
| C(10X) | 135(4) | 1017(4) | 3789(3) | 28(1) |
| C(11X) | 1930(6) | 822(4) | 3496(3) | 38(1) |
| O(12X) | 3425(4) | 1479(3) | 4100(2) | 60(1) |
| O(13X) | 1900(4) | 76(4) | 2690(3) | 72(1) |
| O(1W) | −14195(10) | 347(6) | −1062(5) | 133(2) |

TABLE VII

Observed Bond Lengths [Å] And Angles [°] For Form A Citrate Salt Hydrate.

Bond Lengths

| N(1)—C(2) | 1.308(5) | N(13)—C(14) | 1.506(5) |
|---|---|---|---|
| N(1)—C(6) | 1.366(4) | C(14)—C(15) | 1.525(5) |
| C(2)—C(3) | 1.406(6) | C(15)—C(16) | 1.531(5) |
| C(3)—N(4) | 1.313(5) | C(1X)—O(2X) | 1.244(4) |
| N(4)—C(5) | 1.368(4) | C(1X)—O(3X) | 1.248(4) |
| C(5)—C(6) | 1.412(5) | C(1X)—C(4X) | 1.540(5) |
| C(5)—C(10) | 1.419(5) | C(4X)—O(9X) | 1.414(4) |
| C(6)—C(7) | 1.415(5) | C(4X)—C(5X) | 1.529(5) |
| C(7)—C(8) | 1.370(5) | C(4X)—C(10X) | 1.549(5) |
| C(8)—C(9) | 1.417(5) | C(5X)—C(6X) | 1.511(5) |
| C(8)—C(15) | 1.516(5) | C(6X)—O(7X) | 1.215(4) |
| C(9)—C(10) | 1.364(5) | C(6X)—O(8X) | 1.309(4) |
| C(9)—C(11) | 1.509(5) | C(10X)—C(11X) | 1.510(5) |
| C(11)—C(12) | 1.519(5) | C(11X)—O(13X) | 1.236(5) |
| C(11)—C(16) | 1.527(5) | C(11X)—O(12X) | 1.263(5) |
| C(12)—N(13) | 1.505(5) | | |

Bond Angles

| C(2)—N(1)—C(6) | 117.2(3) | C(12)—N(13)—C(14) | 115.6(3) |
|---|---|---|---|
| N(1)—C(2)—C(3) | 122.4(3) | N(13)—C(14)—C(15) | 111.0(3) |
| N(4)—C(3)—C(2) | 122.3(4) | C(8)—C(15)—C(14) | 110.2(3) |
| C(3)—N(4)—C(5) | 116.5(3) | C(8)—C(15)—C(16) | 101.2(3) |
| N(4)—C(5)—C(6) | 121.3(3) | C(14)—C(15)—C(16) | 108.2(3) |
| N(4)—C(5)—C(10) | 118.8(3) | C(11)—C(16)—C(15) | 100.4(3) |
| C(6)—C(5)—C(10) | 119.9(3) | O(2X)—C(1X)—O(3X) | 126.2(3) |
| N(1)—C(6)—C(5) | 120.2(3) | O(2X)—C(1X)—C(4X) | 117.1(3) |
| N(1)—C(6)—C(7) | 119.1(3) | O(3X)—C(1X)—C(4X) | 116.6(3) |
| C(5)—C(6)—C(7) | 120.6(3) | O(9X)—C(4X)—C(5X) | 111.5(3) |
| C(8)—C(7)—C(6) | 118.2(3) | O(9X)—C(4X)—C(1X) | 109.7(3) |
| C(7)—C(8)—C(9) | 121.2(3) | C(5X)—C(4X)—C(1X) | 112.0(3) |
| C(7)—C(8)—C(15) | 130.8(3) | O(9X)—C(4X)—C(10X) | 108.5(3) |

TABLE VII-continued

Observed Bond Lengths [Å] And Angles [°]
For Form A Citrate Salt Hydrate.

| | | | |
|---|---|---|---|
| C(9)—C(8)—C(15) | 107.9(3) | C(5X)—C(4X)—C(10X) | 109.1(3) |
| C(10)—C(9)—C(8) | 121.6(3) | C(1X)—C(4X)—C(10X) | 105.8(3) |
| C(10)—C(9)—C(11) | 130.4(3) | C(6X)—C(5X)—C(4X) | 118.1(3) |
| C(8)—C(9)—C(11) | 108.0(3) | O(7X)—C(6X)—O(8X) | 122.2(3) |
| C(9)—C(10)—C(5) | 118.4(3) | O(7X)—C(6X)—C(5X) | 125.6(3) |
| C(9)—C(11)—C(12) | 110.2(3) | O(8X)—C(6X)—C(5X) | 112.1(3) |
| C(9)—C(11)—C(16) | 101.9(3) | C(11X)—C(10X)—C(4X) | 113.1(3) |
| C(12)—C(11)—C(16) | 107.8(3) | O(13X)—C(11X)—O(12X) | 123.0(4) |
| N(13)—C(12)—C(11) | 110.8(3) | O(13X)—C(11X)—C(10X) | 120.1(4) |
| | | O(12X)—C(11X)—C(10X) | 116.8(4) |

TABLE VIII

Anisotropic displacement parameters
(Å$^2$ × 10$^3$) For The Form A Citrate Salt Hydrate.
The anisotropic displacement factor exponent takes the form:
$-2\pi^2[h^2 a^{*2}U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| N(1) | 33(2) | 42(2) | 22(2) | 5(2) | 5(2) | 11(2) |
| C(2) | 38(2) | 55(3) | 25(2) | 4(2) | 5(2) | 12(2) |
| C(3) | 52(3) | 36(3) | 34(3) | −5(2) | 1(2) | 5(2) |
| N(4) | 48(2) | 31(2) | 34(2) | −1(2) | 4(2) | 8(2) |
| C(5) | 30(2) | 26(2) | 28(2) | 2(2) | 10(2) | 9(2) |
| C(6) | 26(2) | 33(2) | 19(2) | 7(2) | 7(2) | 9(2) |
| C(7) | 34(2) | 32(2) | 27(2) | 12(2) | 8(2) | 14(2) |
| C(8) | 29(2) | 25(2) | 25(2) | 8(2) | 8(2) | 8(2) |
| C(9) | 24(2) | 30(2) | 23(2) | 7(2) | 9(2) | 10(2) |
| C(10) | 32(2) | 28(2) | 30(2) | 9(2) | 8(2) | 14(2) |
| C(11) | 24(2) | 31(2) | 27(2) | 8(2) | 3(2) | 9(2) |
| C(12) | 26(2) | 31(2) | 26(2) | 10(2) | 2(2) | 4(2) |
| N(13) | 27(2) | 28(2) | 27(2) | 4(1) | 7(1) | 5(1) |
| C(14) | 42(2) | 27(2) | 31(2) | 1(2) | 3(2) | 11(2) |
| C(15) | 35(2) | 25(2) | 28(2) | 9(2) | 3(2) | 3(2) |
| C(16) | 27(2) | 38(2) | 33(2) | 13(2) | 8(2) | 2(2) |
| C(1X) | 18(2) | 22(2) | 32(2) | 6(2) | 4(2) | 5(2) |
| O(2X) | 33(2) | 37(2) | 38(2) | −3(1) | 14(1) | 8(1) |
| O(3X) | 19(2) | 48(2) | 74(2) | −14(2) | 8(1) | 7(1) |
| C(4X) | 18(2) | 17(2) | 26(2) | 2(2) | 1(2) | 2(2) |
| C(5X) | 35(2) | 28(2) | 28(2) | 4(2) | 6(2) | 12(2) |
| C(6X) | 21(2) | 35(3) | 28(2) | 6(2) | 6(2) | 11(2) |
| O(7X) | 47(2) | 28(2) | 39(2) | 8(1) | −5(1) | 10(1) |
| O(8X) | 52(2) | 44(2) | 30(2) | 7(1) | −10(1) | 12(1) |
| O(9X) | 21(1) | 24(1) | 31(1) | 3(1) | 3(1) | 2(1) |
| C(10X) | 19(2) | 31(2) | 39(2) | 12(2) | 7(2) | 11(2) |
| C(11X) | 40(3) | 23(2) | 47(3) | −1(2) | −6(2) | 16(2) |
| O(12X) | 35(2) | 70(2) | 63(2) | −18(2) | 1(2) | 20(2) |
| O(13X) | 59(2) | 88(3) | 66(2) | −16(2) | −3(2) | 42(2) |
| O(1W) | 189(6) | 85(3) | 150(5) | 43(3) | 45(4) | 66(4) |

TABLE IX

Hydrogen Coordinates (×10$^4$) And Isotropic Displacement Parameters
(Å$^2$ × 0$^3$) For Form A Citrate Salt Hydrate.

| | x | y | z | U(eq) |
|---|---|---|---|---|
| H(2) | −10131 | 2752 | −1425 | 80 |
| H(3) | −9580 | 798 | −852 | 80 |
| H(7) | −6566 | 6813 | 747 | 80 |
| H(10) | −5353 | 2838 | 1896 | 80 |
| H(11) | −2677 | 5086 | 3266 | 80 |
| H(12A) | −5374 | 4655 | 4032 | 80 |
| H(12B) | −3939 | 6179 | 4586 | 80 |
| H(13X) | −7310(70) | 5730(60) | 3290(40) | 80 |
| H(13Y) | −6630(70) | 6680(60) | 4340(40) | 80 |
| H(14A) | −4821 | 8605 | 3915 | 80 |
| H(14B) | −6582 | 8031 | 3084 | 80 |
| H(15) | −3834 | 8494 | 2343 | 80 |
| H(16A) | −1613 | 7289 | 2703 | 80 |
| H(16B) | −2059 | 7843 | 3745 | 80 |
| H(5XA) | 713 | 2097 | 2249 | 80 |
| H(5XB) | −1476 | 1523 | 2130 | 80 |
| H(8XX) | −1460(70) | 4290(60) | 920(40) | 80 |
| H(9XX) | 720(70) | 4240(60) | 4480(40) | 80 |
| H(10A) | 193 | 1062 | 4485 | 80 |
| H(10B) | −913 | 162 | 3456 | 80 |
| H(12C) | 4560(70) | 1360(50) | 3770(40) | 80 |
| H(1WX) | −13520(70) | 710(60) | −270(40) | 80 |
| H(1WY) | −14530(80) | −450(60) | −920(40) | 80 |

Figure 3:
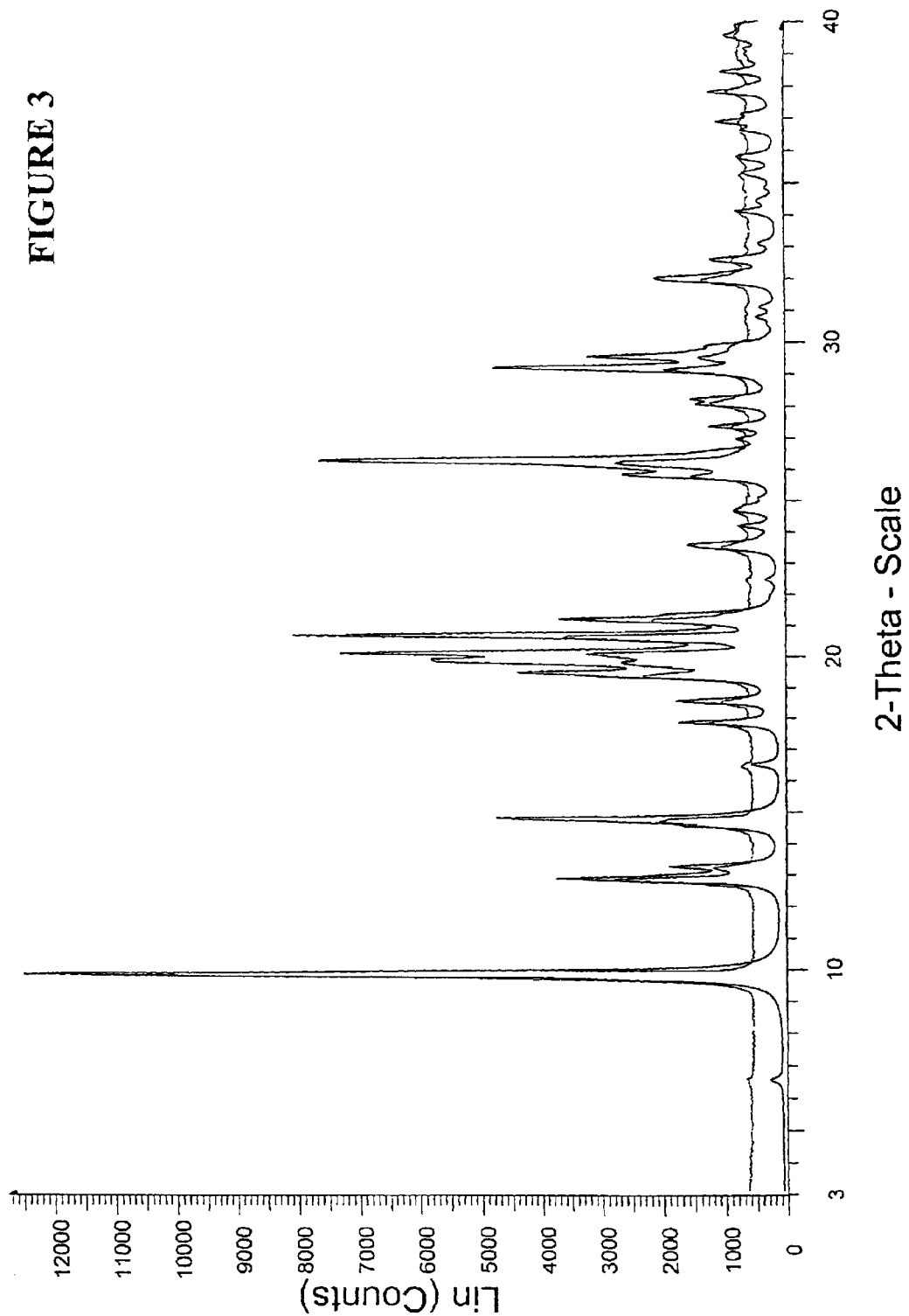
FIG. 3 is the observed X-ray diffraction pattern of 5,8,14-triazatetracyclo[10.3.1.0$^{2,11}$.0$^{4,9}$]-hexadeca-2(11),3,5,7,9-pentaene citrate salt hydrate (Form A) (upper trace) superimposed on the calculated powder X-ray diffraction pattern for Form A (y axis is linear counts per second; X in degrees 2 theta).

The powder X-ray diffraction pattern was calculated from the single crystal data gathered for the citrate salt hydrate Form A via the use of the XFOG and XPOW computer programs provided as part of the SHELXTL™ computer library. The calculated powder pattern for Form A is shown in FIG. 1. A comparison of the observed Form A powder pattern and the calculated pattern results are displayed in the overlaid powder X-ray diffraction pattern of FIG. 3. The lower pattern corresponds to the calculated powder pattern (from single crystal results) and the upper pattern corresponds to a representative experimental powder pattern. The general match between the two patterns indicates the agreement between powder sample and the corresponding single crystal structure.

Solid State NMR

The citrate salt hydrate Form A and the anhydrous or nearly anhydrous Form B were characterized by solid state NMR techniques. For each, approximately 300 mg of a sample was tightly packed into 7 mm ZrO spinner. The $^{13}$C NMR spectra were collected using cross-polarization magic angle spinning (CPMAS) at 295 K on Bruker 7 mm WB MAS probe positioned into a wide-bore Bruker Avance DRX 500 MHz NMR spectrometer. The samples were spun at 7 kHz. The cross-polarization contact time was set to 1 ms. The total of 512 scans were acquired for most of the samples resulting in approximately 30 minute acquisition times. The spectra were referenced using external sample of adamantane with the most upfield methyl signal set to 29.5 ppm.

Figure 6:
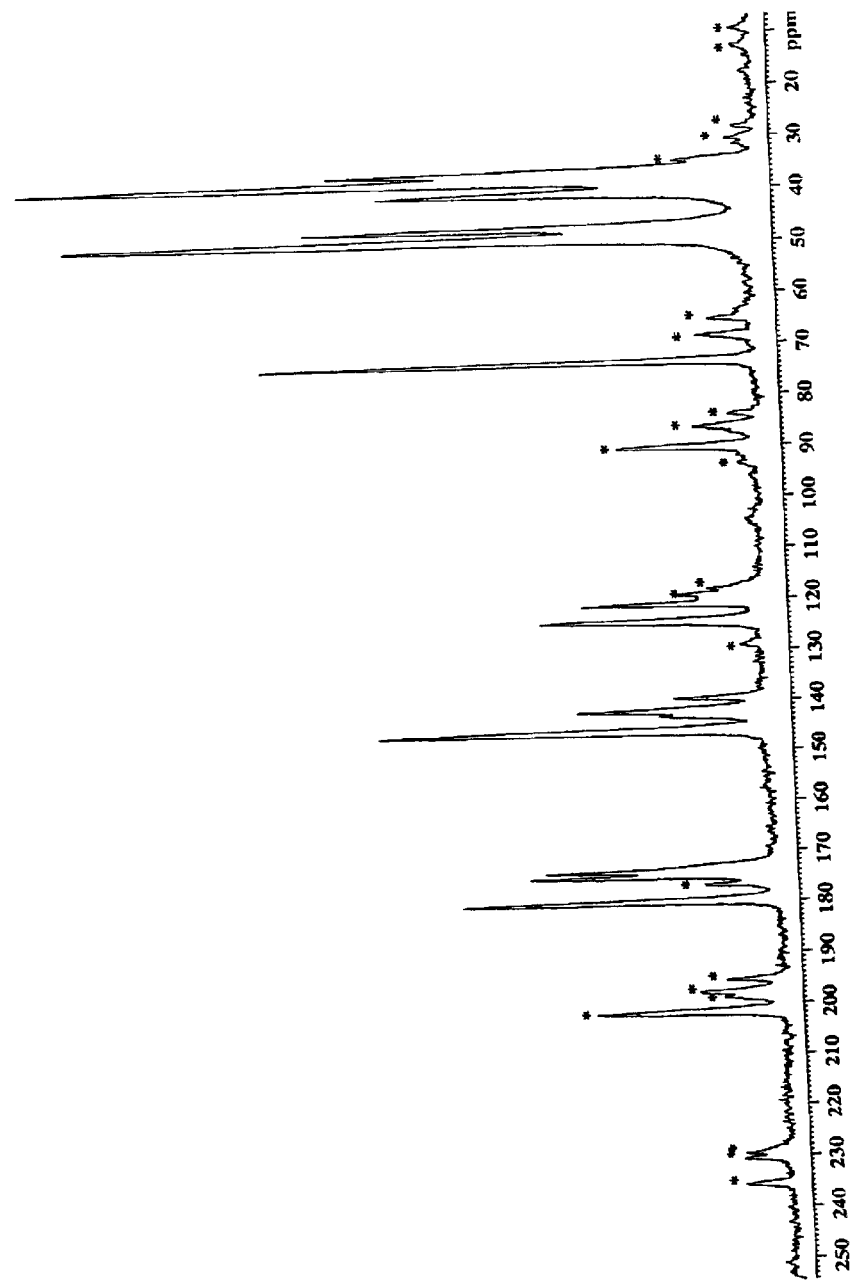
FIG. 6 is the $^{13}$C NMR spectrum of the citrate salt Form A in the solid phase as measured by cross-polarization magic angle spinning (CPMAS) at 295 K on a Bruker 7 mm wide-bore magic angle spinning (WB MAS) probe positioned in a Bruker Avance DRX 500 MHz NMR Spectrometer. Peaks marked with asterisks (*) are spinning sidebands which are displaced at multiples of the spinning frequencies along both sides of the real peaks (centerbands).
Figure 7:
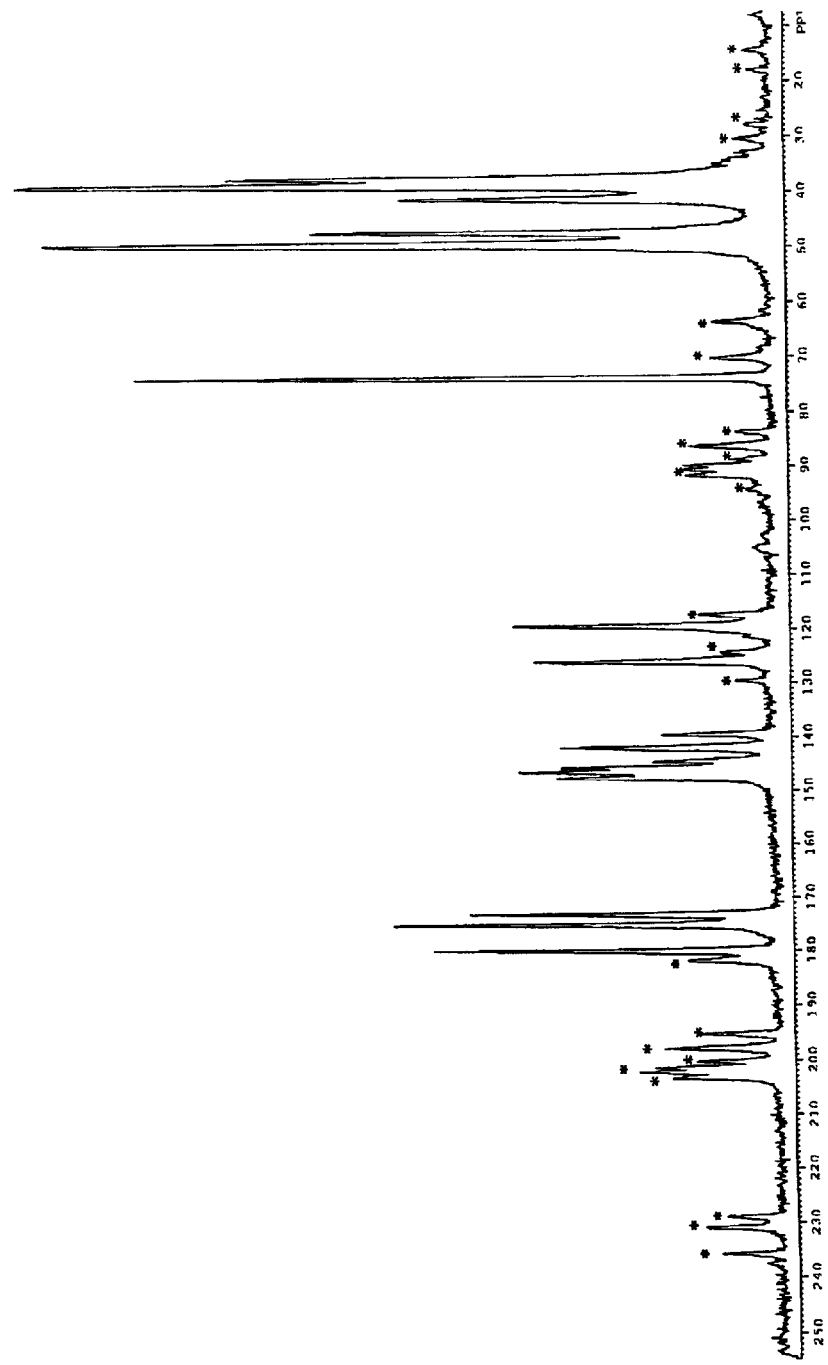
FIG. 7 is the $^{13}$C NMR spectrum of the citrate salt Form B in the solid phase as measured by cross-polarization magic angle spinning (CPMAS) at 295 K on a Bruker 7 mm wide-bore magic angle spinning (WB MAS) probe positioned in a Bruker Avance DRX 500 MHz NMR Spectrometer. Peaks marked with asterisks (*) are spinning sidebands which are displaced at multiples of the spinning frequencies along both sides of the real peaks (centerbands).

The resulting $^{13}$C NMR CPMAS spectrum for Form A is shown in FIG. 6 and Form B in FIG. 7. The samples of the citrate salt polymorphs behaved reasonably well from the point of view of solid state spectra quality. The resolution was good and the sensitivity was acceptable. The spectra features of all the compounds differ substantially from each other suggesting that solid state NMR can easily resolve the minor physical/chemical differences between the samples. All the peaks marked with asterisks (*) are spinning sidebands in FIGS. 6 and 7. The spinning sidebands are displaced at multiple of the spinning frequencies along both sides of the real peaks (centerbands). The spinning speed was set to 7 kHz which at the 500 MHz magnet translates into 55.7 ppm. The sideband intensities depend on the spinning speed (the higher the speed the lower the sideband intensity) and on the size of the anisotropic contribution of the chemical shielding for the given carbon. They can be easily distinguished from centerbands by variable spinning speed experiments. Carbonyl and aromatic sites tend to have very intense sidebands due to their large chemical shielding anisotropies. CH and $CH_2$ type of carbons give origin to relatively small spinning sidebands. Methyl groups ($CH_3$) usually don't generate any sidebands.

The major resonance peaks for the solid state carbon spectrum of 5,8,14-triazatetracyclo[10.3.1.0$^{2,11}$.0$^{4,9}$]-hexadeca-2(11),3,5,7,9-pentaene citrate salt Forms A and B downfield from 100 ppm are listed in Table X.

TABLE X

The Major Solid State $^{13}$C-NMR Resonance Peaks For 5,8,14-triazatetracyclo[10.3.1.0$^{2,11}$.0$^{4,9}$]-hexadeca-2(11),3,5,7,9-pentaene Citrate Salt Forms A and B (Only Peaks Downfield from 100 ppm Listed) (Adamantane Standard 29.5 ppm).

| FORM A $^{13}$C (ppm) Solid | FORM B $^{13}$C (ppm) Solid |
|---|---|
| 179.8 | 180.0 |
| 174.8 | 175.2 |
| 173.7 | 173.1 |
| 145.9 | 142.0 |
| 141.8 | 139.5 |
| 124.1 | 126.1 |
| 120.9 | 119.4 |

The citrate salt of the invention (hereafter "the active salt") can be administered via either the oral, transdermal (e.g., through the use of a patch), intranasal, sublingual, rectal, parenteral or topical routes. Transdermal and oral administration are preferred. The active salt is, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active salt can be administered alone or in combination with pharmaceutically acceptable carriers or diluents by any of the several routes previously indicated. More particularly, the active salt can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active salt is present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active salt in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active salt topically and this can be done by way of creams, a patch, jellies, gels, pastes, ointments and the like, in accordance with standard pharmaceutical practice.

EXAMPLES

The following examples illustrate the methods and compounds of the present invention. It will be understood, however, that the invention is not limited to the specific Examples.

Example 1

Citrate Salt Hydrate of 5,8,14-Triazatetracyclo [10.3.1.0$^{2,11}$.0$^{4,9}$]-Hexadeca-2(11),3,5,7,9-Pentaene (Form A)

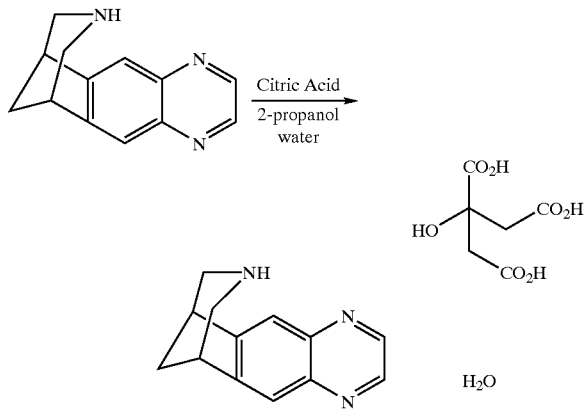

A 200 ml reactor was charged with the free base 5,8,14-triazatetracyclo[10.3.1.0$^{2,11}$.0$^{4,9}$]-hexadeca-2(11),3,5,7,9-pentaene (9 g; 0.047 mol), 2-propanol (90 ml, 10 ml/g) and water (4.5. ml, 0.5 ml/g). The mixture was warmed to 50 to 55° C. to give a solution. The mixture was filtered to remove any specks and fibers present. The clarified solution (at 50 to 55° C.) was treated with a clarified solution of citric acid (11.5 g., 0.0598 mol, 1.4 equiv.) dissolved in water (18 ml) and 2-propanol (18 ml) over about 5 to 15 minutes. The mixture was stirred at 50 to 55° C. for about 1 hour allowing crystallization to occur. The crystal slurry was cooled to 0 to 5° C. over about 1 hour and the final slurry was stirred for about 1 hour. The product was isolated by filtration, washed with 2-propanol (18 ml) and dried at 20 to 30° C. under vacuum for about 24 hours. The identity of Form A was verified by powder x-ray diffraction.

Example 2

Citrate Salt Polymorph of 5,8,14-Triazatetracyclo [10.3.1.0$^{2,11}$.0$^{4,9}$]-Hexadeca-2(11),3,5,7,9-Pentaene (Form B)

The citrate salt hydrate Form A from Example 1 (710.6 g) was jet milled using two passes and dried under vacuum less than 1 hour at 45° C. The particle size reduced citrate hydrate Form A yielded Form B, which was verified by powder X-ray diffraction.

What is claimed is:

1. A polymorphic citrate salt of 5,8,14-triazatetracyclo [10.3.1.0$^{2,11}$.0$^{4,9}$]-hexadeca-2(11),3,5,7,9-pentaene wherein there is between 0 and 5% water by weight present in the crystal.

2. A compound according to claim 1 wherein there is between 1 and 5% water by weight present.

3. A compound according to claim 2 having an x-ray diffraction pattern characterized substantially by an x-ray diffraction pattern peak as measured with copper radiation of a 2θ of about 9.7.

4. A compound according to claim 2 having an x-ray diffraction pattern characterized substantially by the following principal x-ray diffraction pattern peaks expressed in terms of 2θ and d-spacings as measured with copper radiation:

| Angle 2θ | d-value (Å) |
|---|---|
| 9.7 | 9.1 |
| 12.8 | 6.9 |
| 14.6 | 6.1 |
| 19.7 | 4.5 |
| 20.0 | 4.4 |
| 20.5 | 4.3 |
| 26.1 | 3.4 |
| 29.1 | 3.1 |

5. A compound according to claim 2 characterized by an onset of melting/decomposition transition at 167–8° C.

6. A compound according to claim 2 characterized in that when examined by solid state $^{13}$C NMR cross-polarization magic angle spinning techniques it exhibits the following principal resonance peaks: 179.8, 145.9 and 124.1.

7. A compound according to claim 2 characterized in that when examined by solid state $^{13}$C NMR cross-polarization magic angle spinning techniques it exhibits the following principal resonance peaks: 179.8, 174.8, 173.7, 145.9, 141.8, 124.1 and 120.9.

8. A compound according to claim 1 wherein there is between 0 and 1% water present in the crystal.

9. A compound according to claim 8 having an x-ray diffraction pattern characterized substantially by an x-ray diffraction pattern peak as measured with copper radiation of a 2θ of about 9.9.

10. The compound according to claim 8 having an x-ray diffraction pattern characterized substantially by the principal x-ray diffraction pattern peaks expressed in terms of 2θ and d-spacings as measured with copper radiation:

| Angle 2θ | d-value (Å) |
|---|---|
| 9.9 | 9.0 |
| 12.9 | 6.8 |
| 14.6 | 6.1 |
| 19.7 | 4.5 |
| 20.5 | 4.3 |
| 26.1 | 3.4 |

11. A compound according to claim 8 characterized by an onset of melting/decomposition transition at 167–8° C.

12. A compound according to claim 8 characterized in that when examined by solid state $^{13}$C NMR it exhibits the following principal resonance peaks: 180.0, 175.2, 173.1, 126.1 and 119.4.

13. A compound according to claim 8 characterized in that when examined by solid state $^{13}$C NMR it exhibits the following principal resonance peaks: 180.0, 175.2, 173.1, 142.0, 139.5, 126.1 and 119.4.

14. A pharmaceutical composition comprising a compound according to any one of claim 1, 2 or 8 and a pharmaceutically acceptable carrier.

15. A method of treatment for nicotine dependency, addiction or withdrawal in a mammal comprising the administration of a compound according to any of claim 1, 2 or 8 to a subject in need thereof.

16. A process for the preparation of the citrate salt hydrate of 5,8,14-triazatetracyclo[10.3.1.0$^{2,11}$.0$^{4,9}$]-hexadeca-2(11), 3,5,7,9-pentaene according to claim 2 comprising the steps of (i) contacting 5,8,14-triazatetracyclo[10.3.1.0$^{2,11}$.0$^{4,9}$]-hexadeca-2(11),3,5,7,9-pentaene in a suitable solvent with citric acid; and (ii) collecting the crystals formed.

17. A process according to claim 16 wherein the suitable solvent is selected from the group consisting of a (C$_1$–C$_6$) alkyl alcohol, (C$_1$–C$_6$)alkyl ketone and (C$_1$–C$_6$)alkyl ether admixed with water.

18. A process according to claim 16 wherein the suitable solvent is a mixture of acetone and water or 2-propanol and water.

19. A process according to claim 16 wherein the suitable solvent is a mixture of 2-propanol and water.

20. A process according to claim 16 wherein the contacting of step (i) is carried out by contacting 5,8,14-triazatetracyclo[10.3.1.0$^{2,11}$.0$^{4,9}$]-hexadeca-2(11),3,5,7,9-pentaene in solution phase with a solution of citric acid.

21. A process according to claim 16 wherein the contacting step is carried out over a period of between 1 and 24 hours.

22. A process according to claim 16 wherein the contacting step is carried out over a period of between 5 and 15 hours, and comprising stirring or mixing the resulting mixture.

23. A process according to claim 16 wherein the mixture resulting from step (i) is heated to between 30 and 60° C. prior to collection of the crystals.

24. A process for the preparation of an anhydrous or nearly anhydrous citrate salt 5,8,14-triazatetracyclol [10.3.1.0$^{2,11}$.0$^{4,9}$]-hexadeca-2(11),3,5,7,9-pentaene according to claim 8 comprising the step of drying the citrate hydrate of 5,8,14-triazatetracyclo[10.3.1.0$^{2,11}$.0$^{4,9}$]-hexadeca-2(11),3,5,7,9-pentaene.

25. A process according to claim 24 wherein the drying step comprises heating to 60 to 120° C. for between 30 minutes and 24 hours.

26. A process according to claim 25 wherein the heating is for at least 12 hours.

27. A process according to claim 24 wherein the drying step comprises
   (i) reducing the particle size of the citrate hydrate of 5,8,14-triazatetracyclo[10.3.1.0$^{2,11}$.0$^{4,9}$]-hexadeca-2(11),3,5,7,9-pentaene; and
   (ii) placing the resultant solid from step (i) under vacuum.

28. A process according to claim 27 wherein the step (ii) is conducted in the temperature range of between 20 and 60° C.

29. A process according to claim 24 wherein the drying step is effectuated by (i) dissolving Form A in an anhydrous solvent; and (ii) allowing Form B to crystallize from solution.

30. A process according to claim 29 wherein the anhydrous solvent is selected from an anhydrous ($C_1$–$C_6$)alkyl alcohol, a ($C_1$–$C_6$)alkyl ketone, and a ($C_1$–$C_6$)alkyl ether.

31. A process according to claim 29 further comprising the step of driving off the water as an azeotrope after step (i).

32. A process for the preparation of the anhydrous or nearly anhydrous citrate salt of 5,8,14-triazatetracyclo[10.3.1.0$^{2,11}$.0$^{4,9}$]-hexadeca-2(11),3,5,7,9-pentaene according to claim 8 comprising the steps of
   (i) contacting 5.8,14-triazatetracyclo[10.3.1.0$^{2,11}$.0$^{4,9}$]-hexedeca-2(11),3,5,7,9-pentaene with citric acid in an anhydrous suitable solvent; and
   (ii) collecting the crystals formed.

33. A process according to claim 16 wherein the anhydrous suitable solvent is selected from the group consisting of an anhydrous ($C_1$–$C_6$)alkyl alcohol, an anhydrous ($C_1$–$C_6$)alkyl ketone and an anhydrous ($C_1$–$C_6$)alkyl ether.

34. A process according to claim 16 wherein the suitable solvent is anhydrous methanol, anhydrous ethanol or anhydrous 2-propanol.

35. The citrate salt of 5,8,14-triazatetracyclo(10.3.1.0$^{2,11}$.0$^{4,9}$]-hexadeca-2(11),3,5,7,9-pentaene made by the process of claim 16.

36. The citrate salt of 5,8,14-triazatetracyclo[10.3.1.0$^{2,11}$.0$^{4,9}$]-hexadeca-2(11),3,5,7,9-pentaene made by the process of either claim 24 or 34.

* * * * *